(12) United States Patent  (10) Patent No.: US 7,715,522 B2
Goto et al.  (45) Date of Patent: May 11, 2010

(54) X-RAY CT APPARATUS

(75) Inventors: Taiga Goto, Tokyo (JP); Koichi Hirokawa, Tokyo (JP); Osamu Miyazaki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 31 days.

(21) Appl. No.: 12/095,072

(22) PCT Filed: Dec. 25, 2006

(86) PCT No.: PCT/JP2006/325777

§ 371 (c)(1),
(2), (4) Date: May 27, 2008

(87) PCT Pub. No.: WO2007/074772

PCT Pub. Date: Jul. 5, 2007

(65) Prior Publication Data

US 2009/0245459 A1 Oct. 1, 2009

(30) Foreign Application Priority Data

Dec. 28, 2005 (JP) .............................. 2005-378521

(51) Int. Cl.
*G01N 23/00* (2006.01)
(52) U.S. Cl. .............................. 378/16; 378/8; 378/901
(58) Field of Classification Search ............... 378/4–20, 378/91, 95–97, 114–117, 901
See application file for complete search history.

(56) References Cited

U.S. PATENT DOCUMENTS 6,778,628 B2 8/2004 Yamazaki et al.

FOREIGN PATENT DOCUMENTS

JP 2004-97778 4/2004

*Primary Examiner*—Jurie Yun
(74) *Attorney, Agent, or Firm*—Cooper & Dunham LLP

(57) ABSTRACT

An X-ray CT apparatus inputs information with respect to a target tissue of the object to be discriminated in the tomographic image and inputs an index with respect to correctness of the discrimination, and determines scanning conditions for discriminating the target tissue based on the index.

20 Claims, 11 Drawing Sheets

X-RAY CT APPARATUS

TECHNICAL FIELD

This disclosure relates to an X-ray CT apparatus and, in particular, relates to an improvement in an X-ray CT apparatus that has a function of aiding setting of many parameters to be set at a scanning planning stage prior to a scanning when performing an existence diagnosis of a lesioned portion, for example, a cancer in an organ of an object to be examined.

CONVENTIONAL ART

Since a contrast, amount of noises and a discrimination capacity of an image of a lesioned portion representing a target tissue with respect to a background tissue displayed on a display of an X-ray CT apparatus vary complexly in association with such as scanning conditions to be set (such as tube voltage, tube current, circumferential rotation speed, helical pitch and slice thickness), reconstruction conditions (such as reconstruction filters) and size of the target tissue, it was difficult to estimate a quality of images of the target tissue to be produced and to determine optimum parameters to be set at a scanning planning stage prior to a scanning.

JP-A-2004-97778 discloses an X-ray computer tomographic scanning apparatus comprising a plan assisting system for resolving such problem that includes a condition optimizing function as well as a scan planning screen building function having a graphical user interface (GUI). Wherein, the apparatus is constituted so as to assist a scanning planning in such a manner that when a dose represented by CTDI (CT Dose Index) is inputted on the scan planning screen having GUI, a DEI (Dose Efficiency Index) showing a target diameter having 50% detection rate (discrimination rate) on a reconstructed image and its phantom sample image corresponding thereto are displayed on the scan planning screen, and further, when a desired detection rate, target diameter or density difference between a target tissue defined by a target diameter and its background tissue are inputted, a target diameter, detection rate or DEI corresponding thereto is displayed on the scan planning screen.

However, when the energy (a tube voltage) for X-ray irradiation varies, the CT value of the target tissue for scanning and the CT value of the background tissue around the target tissue vary and the difference of the CT values, namely the contrast varies at the same time. Since the DEI shows a characteristic which varies in response to the contrast, when taking into account of such influences due to contrast, it is necessary to prepare a data base provided with many DEI characteristics for every contrasts. Since the data base provided with such DEI characteristics has to be prepared for every apparatus by making use of a phantom, many man hours are required therefor and at the same time since the DEI characteristics in the data bases are significantly affected by characters of individual evaluators on the target diameters, the level of user friendliness of the apparatus differs depending on experiences of users using the apparatus thereafter.

BRIEF SUMMARY

In an aspect of this disclosure, there is provided an X-ray CT apparatus having a versatile function in which only by setting limited numbers, of simple parameters to be set at a scanning planning stage prior to a scanning, the setting of other parameters to be set is aided.

More specifically, in an X-ray CT apparatus provided with an X-ray generating means, an X-ray detector disposed opposing to the X-ray generating means, a rotating means for rotating the X-ray generating means and the X-ray detector on a circular orbit of a same rotation center, a control means for controlling so as to irradiate X-rays from the X-ray generating means to an object laid along the rotation center and to detect by the X-ray detector X-ray dose penetrated through the object while rotating the X-ray generating means and the X-ray detector through the rotating means and a reconstruction computing means for performing reconstruction computation by making use of the data of the penetrated X-ray dose obtained under the control of the control means and acquiring a tomographic image, the X-ray CT apparatus according to another aspect of this disclosure is further provided with an input means being inputted of information with respect to an target tissue of the object to be discriminated in the tomographic image and of an index with respect to correctness of the discrimination, and a scanning condition determining means for determining scanning conditions for discriminating the target tissue based on the index inputted by the input means. Further, a scanning condition determining method for an X-ray CT apparatus, the scanning condition determining method for an X-ray CT apparatus according to another aspect of this disclosure is provided with, (1) the step of inputting information with respect to an target tissue to be discriminated in a tomographic image to be acquired by the X-ray CT apparatus and an index with respect to correctness of the discrimination, and (2) the step of determining scanning conditions for discriminating the target tissue with the index based on the information with respect to the target tissue, the index and apparatus characteristics of the X-ray CT apparatus.

According to another aspect of this disclosure, an X-ray CT apparatus having a versatile function is provided in which by setting limited numbers of simple parameters to be set at a scanning planning stage prior to a scanning, the setting of other parameters to be set is aided.

According to another aspect of this disclosure, by inputting simple input items through an input device at a scanning planning stage prior to a scanning, even a user with less experience of the X-ray CT apparatus can easily acquire an image having of a desired quality by the user with regard to a visibility (recognition capability).

BEST MODE FOR CARRYING OUT THE INVENTION

Herein below, a preferred embodiment of an X-ray CT apparatus according to the present invention will be explained with reference to the accompanied drawings.

Figure 1:
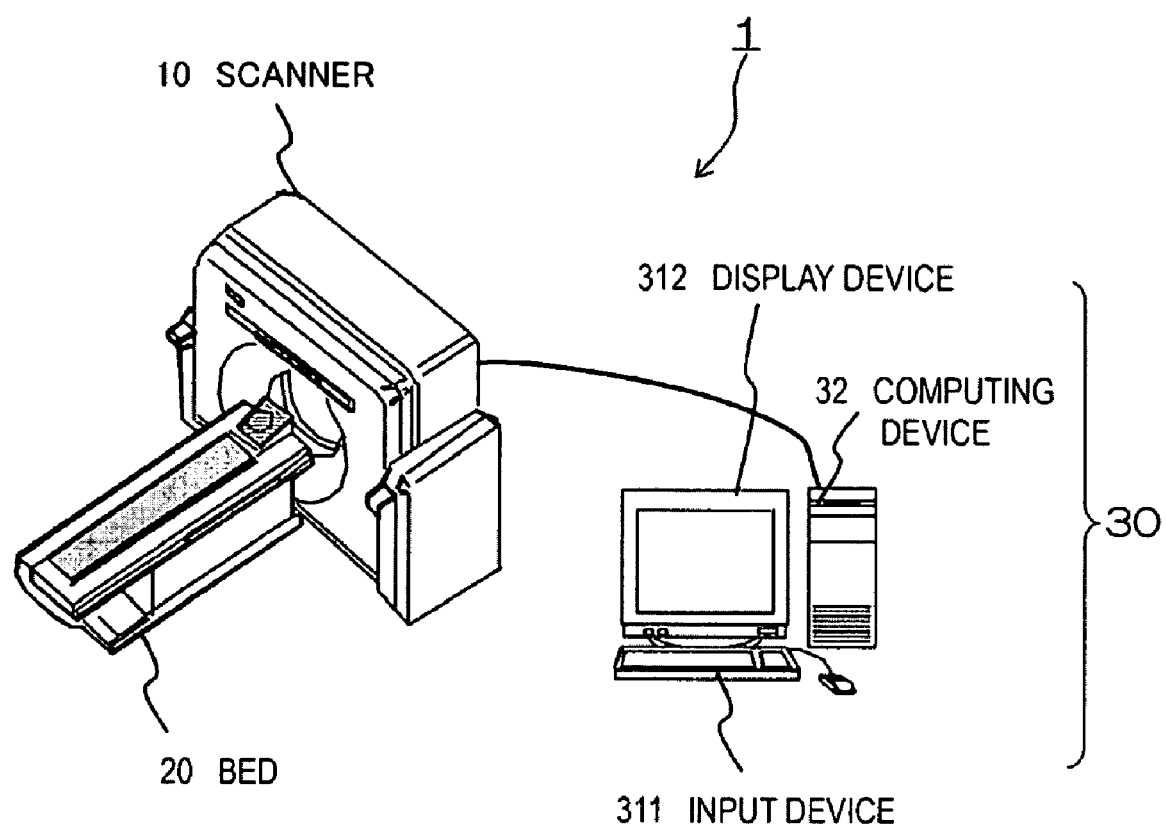
FIG. 1 is an outlook of an X-ray CT apparatus to which the present invention is applied.

FIG. 1 is a schematic diagram showing an outlook of an X-ray CT apparatus 1 to which the present invention is applied, and which is constituted by a scanner 10 used for scanning, a bed 20 for laying an object 40 (see FIG. 2) and moving the same and an operation unit 30 including an input device 311 that is constituted by such as a mouse and a keyboard and is for inputting measurement and reconstruction parameters such as bed moving speed information and reconstruction position, a computing device 32 that processes (including reconstruction) data obtained from a detector 12 (see FIG. 2) and a display device 312 that displays reconstructed images.

Figure 2:
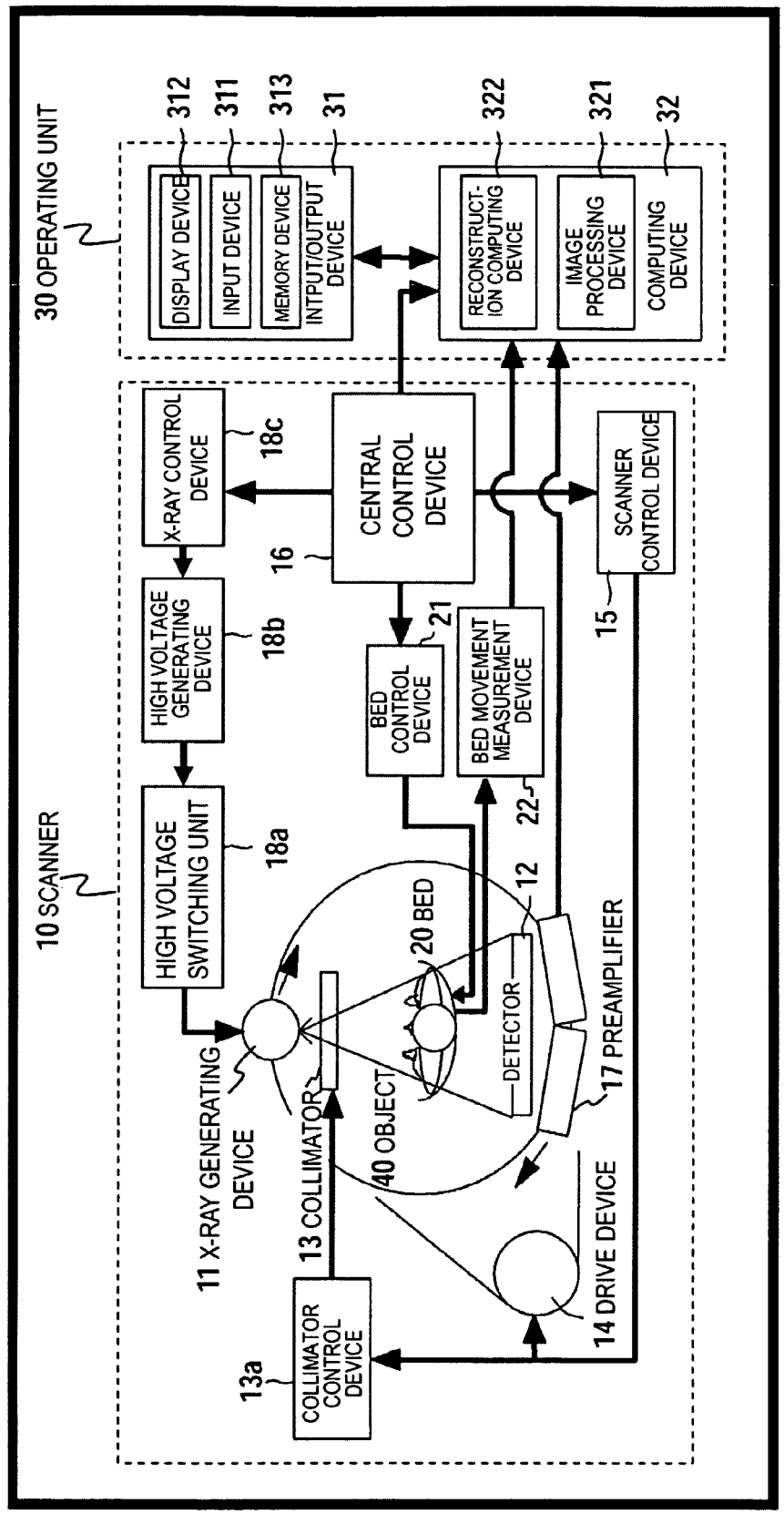
FIG. 2 is an entire constitutional diagram of the X-ray CT apparatus as shown in FIG. 1.

FIG. 2 is an entire constitutional diagram of the X-ray CT apparatus 1 as shown in FIG. 1, of which scan system is a rotate-rotate system (third generation) and that is primarily constituted by the scanner 10, the bed 20 and the operation unit 30 as explained above.

The scanner 10 is constituted by such as an X-ray generation device 11, a high voltage switching unit 18a, a high voltage generation device 18b, an X-ray control device 18c, the X-ray detector 12, a preamplifier 17, a collimator 13, a collimator control device 13a, a drive device 14 that rotatably drives the X-ray generation device 11 and the X-ray detector 12, a scanner control device 15 that controls the drive device 14 and the collimator control device 13a, a bed control device 21 that performs elevation of the bed 20 and movement control in a body axial direction, a bed movement measurement device 22 that measures the amount of movement of the bed 20 and a central control device 16 for controlling the scanner 10 and the operation unit 30.

The operation unit 30 is provided with an input and output device 31 and the computing device 32. The input and output device 31 is provided with the input device 311 constituted of a mouse and a keyboard, the display device 312 constituted of a monitor displaying such as reconstructed images and the memory device 313 constituted of a display memory, a main memory and a hard disk such as for storing display data such as the reconstructed images to be displayed on the display device 312 and for storing a reconstruction program. The computing device 32 is provided with an image processing means 321 that performs image processings such as a preprocessing, a filtering processing and a post processing based on projection data sent from the scanner 10 and a reconstruction computing device 322 for reconstructing the above projection data.

From the input device 311 in the operation unit 30 are inputted such as device conditions (such as a target angle, a target material and a target density of the X-ray tube, an aluminum equivalent of characteristic X-ray filtering of the X-ray tube, a scintillator material, a scintillator density, a scintillator thickness, a shape of bow tie filter, material of the bow tie filter and a shape of copper filter), information on inspection portion of scanning object (target tissue of inspection portion, size thereof and recognition rate thereof), scanning conditions (such as tube current, tube voltage, circumferential rotating speed and helical pitch), reconstruction conditions (image FOV, reconstruction filter, slice thickness of image and slice position to be reconstructed) and reference information (such as CT values or difference of the CT values of an target tissue and a background tissue of every inspection portions at a standard scanning condition or densities of an target tissue and a background tissue and X-ray attenuation characteristics of respective target tissue and background tissue, and based on the indications control signals necessary for the scanning are sent from the central control device 16 to the X-ray control device 18c, the bed moving device 21 and the scanner control device 15 and after receiving a scanning start signal a scanning operation begins. Further, such as the device conditions and the reference information are inputted in advance via the input device 311 and are stored in the memory device 313. When a scanning operation begins, a control signal is sent from the X-ray control device 18c to the high voltage generation device 18b, a high voltage is applied to the X-ray generation device 11 via the high voltage switching unit 18a and X-rays are irradiated from the X-ray generation device 11 to the object 40. At the same time, a control signal is sent from the scanner control device 15 to the drive device 14 and the X-ray generation device 11, the X-ray detector 12 and the preamplifier 17 are rotated around the object 40.

On the other hand, the bed 20 laying the object 40 is caused by the bed control device 21 to be standing still (at the time of circular scanning) or to move (at the time of helical scanning) in the circumferential rotation axis of such as the X-ray generation device 11. The X-rays irradiated are restricted by the collimator 13 of its irradiation region, are absorbed (attenuated, weakened), penetrate through the object 40 and are detected by the X-ray detector 12. The X-rays detected by the X-ray detector 12 are converted into current, are amplified by the preamplifier 17 and are inputted into the computing device 32 as a projection data signal. The projection data signal inputted to the computing device 32 is subjected to image reconstruction processing at the reconstruction computing device 322 in the computing device 32. The reconstructed image is stored in the memory device 313 within the input and output device 31 and is displayed on the display device 312 as a CT image.

Figure 3A:
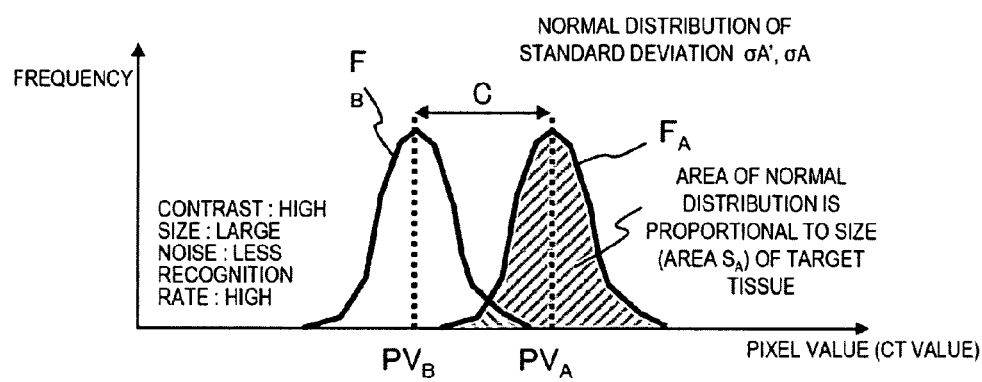
FIGS. 3(a) and 3(b) are diagrams for explaining a principle applied in the present invention.
Figure 3B:
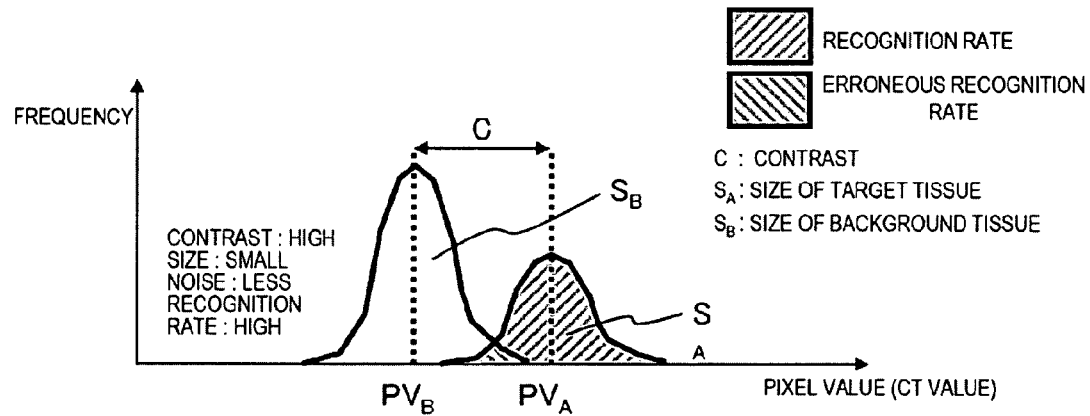

When plotting distributions of pixel values (CT values) of an target tissue of an inspection portion, for example, a contrast study processed cancer in a liver and of a background tissue surrounding the same that are displayed on the display device in the X-ray CT apparatus, the plotting shows normal distributions as shown in FIG. 3(*a*) and FIG. 3(*b*). Herein, respective peak values $PV_A$, $PV_B$ in the normal distribution curve $F_A$ of the target tissue A and the normal distribution curve $F_B$ of the background tissue B respectively correspond to average CT values of the target tissue A and the background tissue B, accordingly, the difference between $PV_A$, $PV_B$, namely the CT value difference corresponds to the contrast between the target tissue A and the background tissue B, further, the respective standard deviation $\sigma_A$, $\sigma_B$ in the normal distribution curve $F_A$ of the target tissue A and the normal distribution curve $F_B$ of the background tissue B respectively correspond to the amount of noises in the target tissue A and the background tissue B, further, areas $S_A$, $S_B$ obtained by integrating the respective curves and converted into pixel number respectively correspond to the sizes of the target tissue A and the background tissue B, and further, the ratio (area ratio) of a portion (namely, a portion in the normal distribution of the target tissue A not overlapping with the normal distribution of the background tissue B) excluding the overlapping portion of the normal distribution curve $F_A$ of the target tissue A over the normal distribution curve $F_B$ of the background tissue B with respect to the entire normal distribution of the target tissue A corresponds to a discrimination capability, namely, a recognition rate D. Further, although FIG. 3(*a*) shows an instance where the sizes of the target tissue A and the background tissue B are substantially the same and FIG. 3(*b*) shows an instance where the size of the target tissue A is comparatively small with respect to the size of the background tissue B, in the present invention the size of the background tissue B is selected substantially the same as the size of the target tissue A.

As seen from FIG. 3(*a*) and FIG. 3(*b*), the recognition rate D of the target tissue A varies, when sizes $S_A$, $S_B$ of the target tissue A and the background tissue B, the contrast C between the target tissue A and the background tissue B and the standard deviation $\sigma_A$, $\sigma_B$ corresponding to the amount of noises of the target tissue A and the background tissue B are modified, namely, D is conceptually expressed by the following function;

$$D=f(S_A,S_B,C,\sigma_A,\sigma_B)$$

FIG. 4(*a*), FIG. 4(*b*) and FIG. 4(*c*) are schematic illustrations of the above concept.

FIG. 4(*a*) is a discrimination capability characteristic with respect to contrast. Near a low contrast, the recognition rate is low due to the effect of noises, but when the contrast rises comparatively high, the recognition rate suddenly enhances, and when the contrast further rises, the recognition rate becomes constant (100%).

FIG. 4(*b*) is a discrimination capability characteristic with respect to noises. When the noises are extremely low with respect to the contrast, the recognition rate is high even if the noises increase some, but when the noises increase to a certain level, the recognition rate suddenly lowers, and when the noises further increase, the recognition rate become constant (0%).

FIG. 4(*c*) is a discrimination capability characteristic with respect to size. When the size is small, the recognition rate is low due to the effect of noises, but when the size increases to a certain degree, the recognition rate suddenly enhances, and when the size further increases, the recognition rate becomes constant (100%). When the contrast increases, the recognition rate is high even if the size is small, and when the noises increase, the recognition rate lowers when the size is small.

In the present invention, an X-ray CT apparatus having a function of aiding setting of parameters to be set by a user at a scanning planning stage prior to a scanning is constructed by making use of the relationship between the recognition rate D of the target tissue A, the sizes $S_A$, $S_B$ of the target tissue A and the background tissue B, the contrast C between the target tissue A and the background tissue B and the standard deviation $\sigma_A$, $\sigma_B$ corresponding to the amount of noises of the target tissue A and the background tissue B.

In the present embodiment, a sequence of scanning planning prior to a scanning will be explained herein below along with FIG. 5 and with reference to FIGS. 3-4 and FIGS. 6-11 by taking up an example wherein a liver of the object 40 is assumed as the scanning target inspection portion and a possible existence in the target tissue of a cancer exceeding 2 cm is diagnosed by making use of contrast medium.

In step S1, a user at first inputs a cancer exceeding 2 cm possibly formed in the liver as an target tissue A in the scanning target inspection portion from the input device 311, and further inputs a recognition rate, for example, 80% representing an index value of a desired image quality. When these are inputted, a corresponding background tissue B and the size of the background tissue B corresponding to the inputted size of the target tissue A are read out from the data base of the memory device 313.

Figure 6:
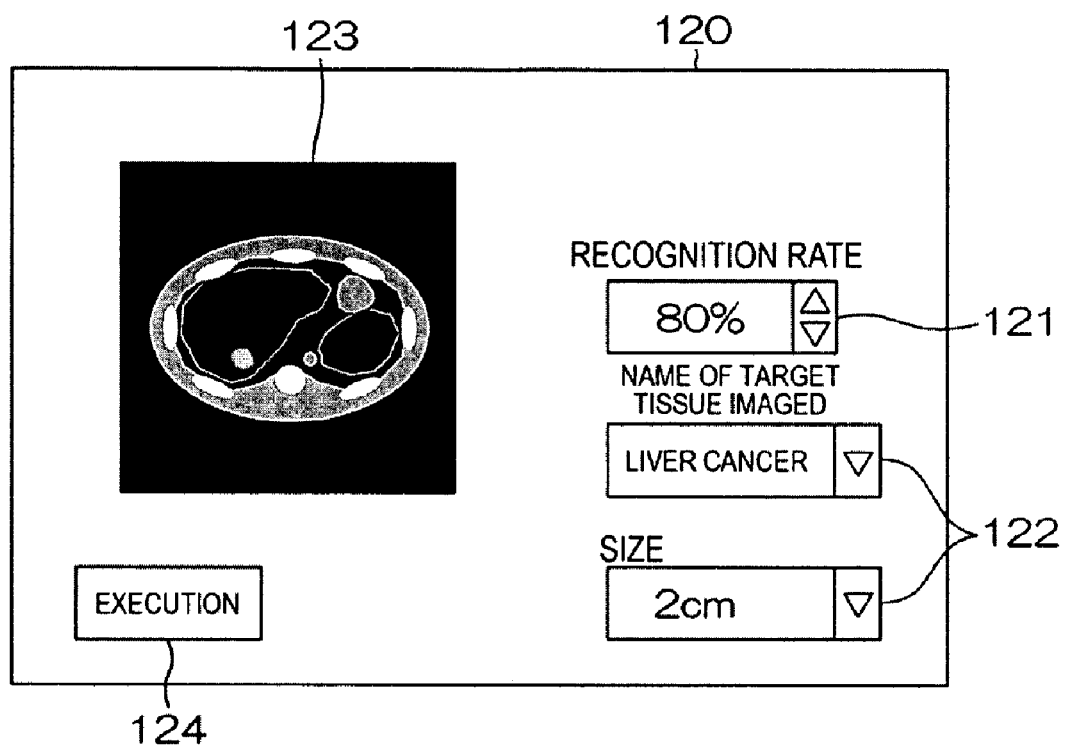
FIG. 6 is an exemplary display on a display device of an input content with regard to a target tissue of the inspection portion inputted via an input device in FIG. 2 and a presumed reconstruction image of the inspection portion containing the target tissue resulted from the computation executed by the computing device according to the input content likely at the scanning planning stage prior to an actual scanning of the inspection portion of the object according to the present invention.

FIG. 6 is a display example displayed at that moment on the screen 120 of the display device 312 wherein in a recognition rate field 121 and scanning target tissue name and size fields 122 at the right side, the respective inputted information is displayed, and a tomographic image 123 at the left side, which is displayed after executing the computation based on these inputs as will be explained below, is a presumed reconstruction image of the inspection portion including the target tissue A and the background tissue B having the inputted recognition rate 80% for the user evaluation.

In the data base of the memory device 313, sizes of background tissue corresponding to the sizes of target tissue for every inspection portions, X-ray attenuation characteristics and densities of both tissues and CT values of target tissue and background tissue for every inspection portions under the standard scanning condition are stored.

Figure 7:
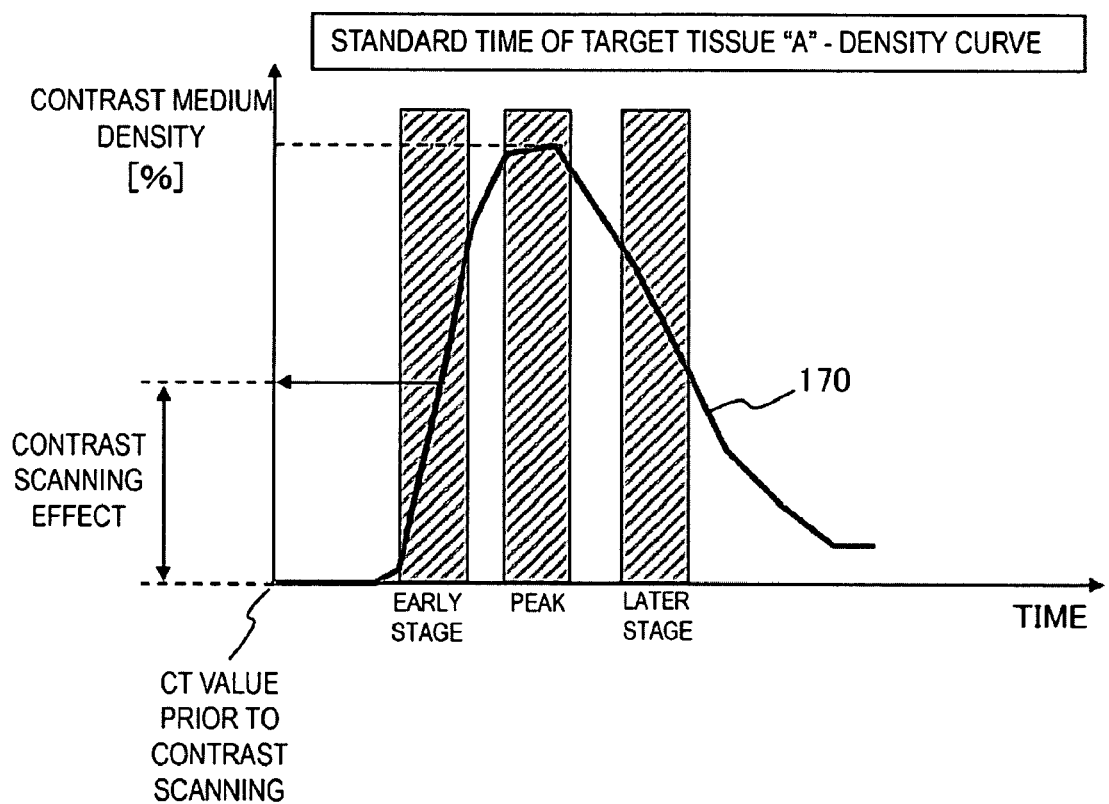
FIG. 7 is an example of standard time and density curves, which are stored in the memory device in FIG. 2 according to the present invention, representing contrast medium density for every target tissue in respective inspection portions of a standard human body when the laps time after injecting contrast medium during a contrast study is used as a parameter.

Further, in the data base of the memory device 313, are stored as shown in FIG. 7 standard time and density curves representing contrast medium density for every target tissue in respective inspection portions of a standard human body using as a parameter lapse time from injection of contrast medium to the object during contrast scanning inspection of the target tissue using a contrast medium (iodine), and X-ray attenuation characteristics at respective densities. The respective standard time and density curves are displayed on the display device 312 during contrast scanning inspection depending on necessity of a user and are used when the user determines a timing of contrast scanning, namely, contrast scanning phases such as early stage of image contrasting, peak stage and late stage of image contrasting depending on such as image contrasting conditions (such as injection speed and injection amount) and body type of the object.

In step S2, effective spectrum of irradiation X-rays and effective X-ray energy for every tube voltages irradiated from the X-ray generation device 11 to the target tissue A and the background tissue B set in step S1 and detected by the detector 12 are calculated.

Further, the calculation of the effective spectrum of irradiation X-rays for every tube voltages and respective X-ray energies can be performed in advance and the result thereof can be stored in advance in the data base of the memory device 313.

Figure 8:
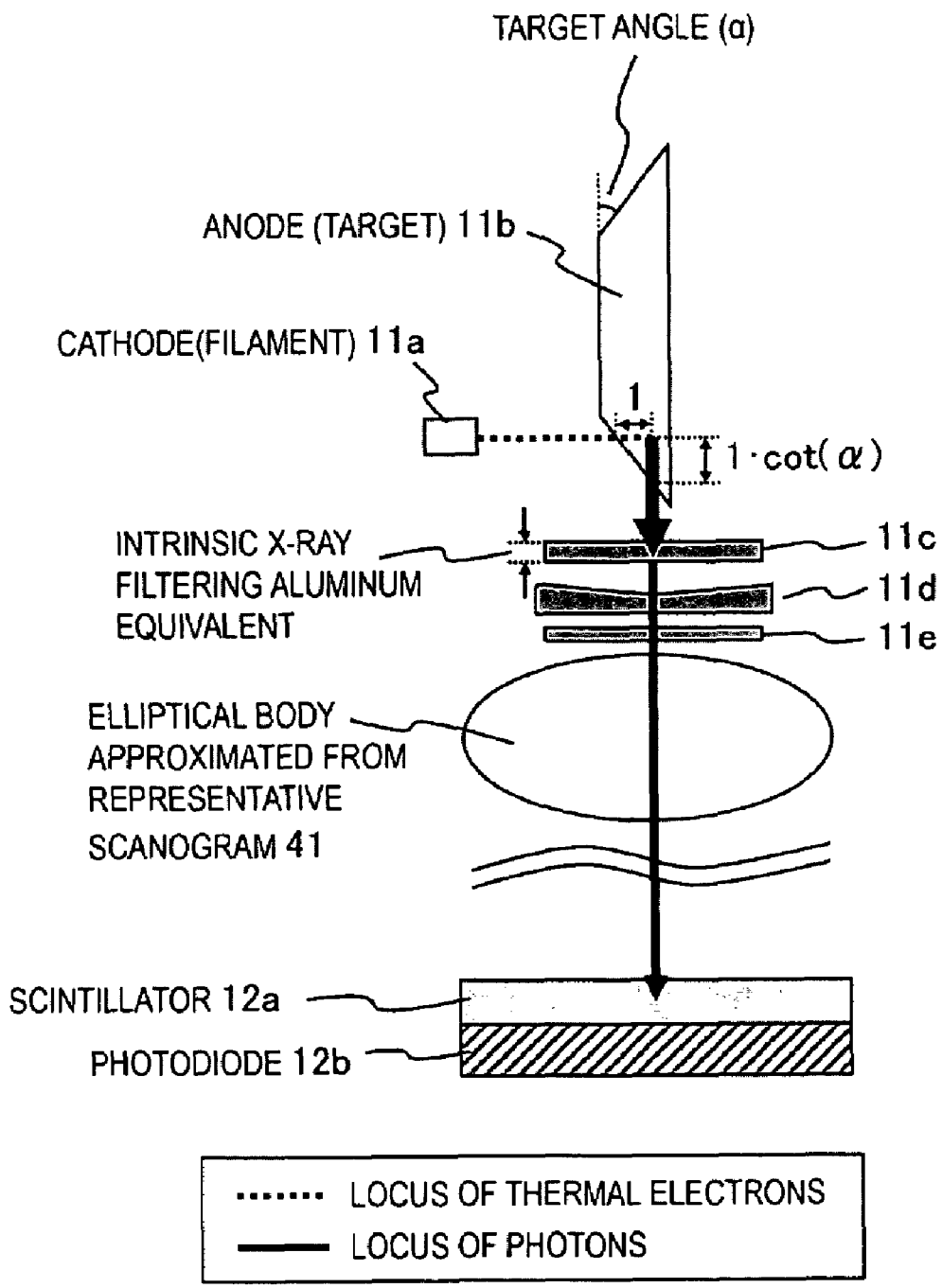
FIG. 8 is a diagram for explaining attenuation of X-rays until being detected by the opposing detector after being generated from the X-ray generation device in FIG. 2.

FIG. 8 is a diagram for explaining the effective X-ray spectrum, effective X-ray energy generated from the X-ray generation device 11 and detected by the opposing detector 12 and attenuation thereof. In step S2, spectrum of bremsstahlung X-rays and spectrum of characteristic X-rays are respectively estimated from equations 1 and 2 based on the device conditions and the scanning conditions, and the spectrum of irradiation X-rays is estimated through the combination thereof.

$$I_E = N\rho/A \int_E^{T_0} (l+T/m_0 c^2) Q(dT/dl)^{-1} \exp(-\mu(E)l_t \cot\alpha) dT \tag{1}$$

$$I_{ch} \propto (T_0/T_{K,L})^{1.63} \tag{2}$$

Wherein, $I_E$ is the energy intensity of bremsstahlung X-rays having photon energy E (=hμ), $I_{ch}$ is the energy intensity of the characteristic X-rays, N is Avogadro number, ρ, A are respectively density and atomic weight of the target, $m_0$ is weight of an electron, c is velocity of light, $T_0$ is an energy of an incident electron, Q is an energy intensity of X-rays emitted from one electron and is a value determined approximately by the ratio of photon energy E/electron energy T, dT/dl a theoretical formula with regard to stopping power proposed such as by Bethe, et al. $l_t$ is a penetration depth of electron and $T_{K,L}$ is an energy necessary for removing an electron from K, L electron orbits. Further, for the calculation of X-ray spectrum, already known other methods can be used.

As shown in FIG. 8, thermo electrons are irradiated from a cathode (filament) 11a to an anode (target) 11b with a target angle α and photons produced at the target 11b are generated in substantially vertical angle with respect to the incident angle of the thermo electrons. The photons penetrate through an characteristic filtering aluminum equivalent 11c, a compensating filter (bow tie filter) 11d and a copper filter 11e, the effective spectra of X-rays to be irradiated to the inspection portion including the target tissue and the background tissue of the object are calculated while taking into account of such irradiation passage of the X-rays, the photons further penetrate through an X-ray absorbing body such as an elliptical body converted equivalent to water and produced as a pseudo object from a scanogram taken at an initial scanning planning stage and make incidence to a scintillator 12a where the same are converted into light. The converted light is detected by a photodiode 12b.

From the calculated effective spectra of the irradiated X-rays, ratios of every energies with respect to all of the spectra as contribution rates, and effective energies are calculated based on the calculated contribution rates.

Figure 9:
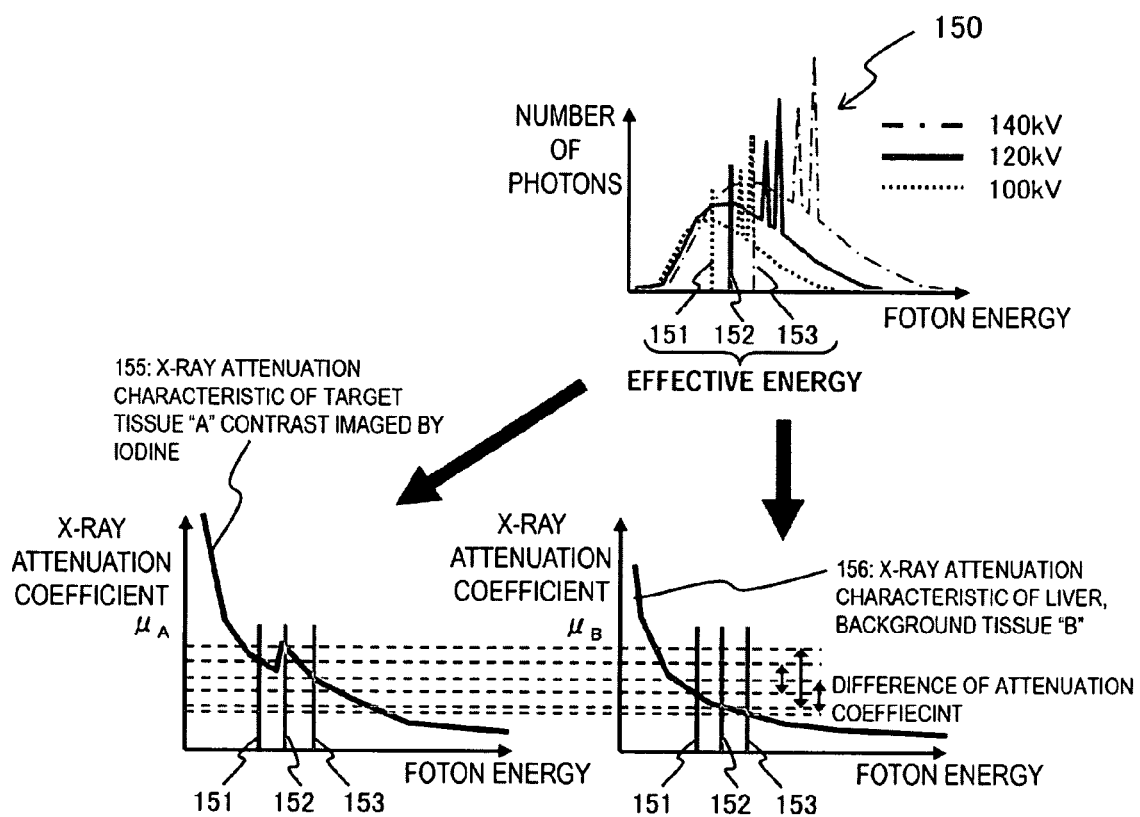
FIG. 9 is a diagram for explaining effective energies of X-rays corresponding to effective spectra of irradiation X-rays for every tube voltage in the X-ray generation device, respective X-ray attenuation coefficients corresponding thereto of contrast scanning processed target tissue and background tissue, contrasts between the target tissue and background tissue corresponding to the set of X-ray attenuation coefficients for respective corresponding tube voltages and setting of tube voltage based on the respective contrasts as referred to in the flowchart in FIG. 5.

FIG. 9 is a diagram for explaining the setting of tube voltage at step S3, wherein respective X-ray attenuation coefficients are at first determined from the effective energies at respective tube voltages determined in step S2 and the X-ray attenuation characteristics of the target tissue and the background tissue of the corresponding inspection portion at the time of contrast scanning under a certain contrast medium density which are stored in the data base within the memory device 313, are compared each other and a tube voltage is selected at which the difference between the X-ray attenuation coefficients of the target tissue and the background tissue is maximized.

Graphs 150 in FIG. 9 are graphs in which distributions of effective spectra of the irradiation X-rays obtained at the times of tube voltages of 100 kv, 120 kv and 140 kv are respectively illustrated by a dotted line, solid line and dashed line. While performing the processing in step S2 by making use of the distribution of the effective spectra of the irradiation X-rays at the respective tube voltages, effective energies for every tube voltages 151, 152 and 153 (corresponding respectively to 100 kv, 120 kv and 140 kv) are calculated.

Graphs 155 and 156 in FIG. 9 show graphs of which vertical axis represents X-ray attenuation coefficient (μA) of the target tissue and X-ray attenuation coefficient (μB) of the background tissue that are contrast imaged with a contrast medium (iodine) having a certain density and of which horizontal axis is X-ray attenuation characteristics as defined as photon energy. After determining cross points of the X-ray attenuation characteristic of graph 155 with the respective effective energies 151, 152 and 153 and cross points of the X-ray attenuation characteristic of graph 156 with the respective effective energies 151, 152 and 153, a tube voltage corresponding to an effective energy showing the largest difference between the graphs 155 and 156 of the respective effective energies, namely, the largest difference of the X-ray attenuation coefficients is selected. In FIG. 9, tube voltage of 120 kv corresponds to the largest difference of the X-ray attenuation coefficients.

Further, as an alternative, the apparatus can be constituted in such a manner that while causing to display the X-ray attenuation characteristic $\mu_A$ Of graph 155 and the respective effective energies 151, 152 and 153 and the X-ray attenuation characteristic $\mu_B$ of graph 156 and the respective effective energies 151, 152 and 153 on the display device 312, and when a user clicks a desired effective energy, a tube voltage corresponding thereto is selected. Thereby, after the user recognizes the difference of the X-ray attenuation coefficients, the user can select an effective energy under a desired condition such as putting priority on low exposure rather than recognition capability.

Step S4 is a step that is executed in a case where densities $D_A$, $D_B$ of the target tissue A and the background tissue B in the inspection portion are not stored in the database within the memory 313, for example, as in the present embodiment where the target tissue is contrast imaged by making use of a contrast medium. When the densities $D_A$, $D_B$ of the target tissue A and the background tissue B in the inspection portion are stored in the database within the memory 313, this step is omitted.

In step S4, densities $D_A$, $D_B$ of the target tissue A of contrast study and the background tissue B corresponding thereto are calculated by making use of CT values $PV_A$, $PV_B$ of the target tissue A of contrast scanning and the background tissue B corresponding thereto under a standard scanning condition (for example, tube voltage of 120 kv) which are stored in the database within the memory device 313, their attenuation coefficients $\mu_A$, $\mu_B$ and an attenuation coefficient of water $\mu_W$ under the same condition and according to the following formulas 3-1 and 3-2;

$$PV_A = (D_A \mu_A - \mu_W) \cdot 1000/\mu_W \tag{3-1}$$

$$PV_B = (D_B \mu_B - \mu_W) \cdot 1000/\mu_W \tag{3-2}$$

In step S5, by making use of the densities $D_A$, $D_B$ of the target tissue A of contrast scanning and the background tissue B calculated at step S4, the attenuation coefficients $\mu_A$, $\mu_B$ corresponding to the tube voltage selected at step S3 and the attenuation coefficient of water $\mu_W$ under the same condition and according to the following formula a contrast C (difference of the CT values) between the target tissue A of contrast scanning and the background tissue B in the inspection object is calculated;

$$C = (D_A \mu_A - D_B \mu_B) \cdot 1000 / \mu_W \quad (4)$$

Figure 4A:
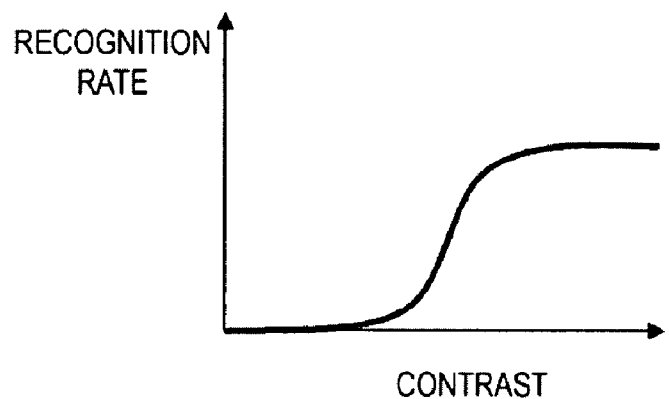
FIGS. 4(a), 4(b) and 4(c) are also diagrams for explaining a principle applied in the present invention.
Figure 4B:
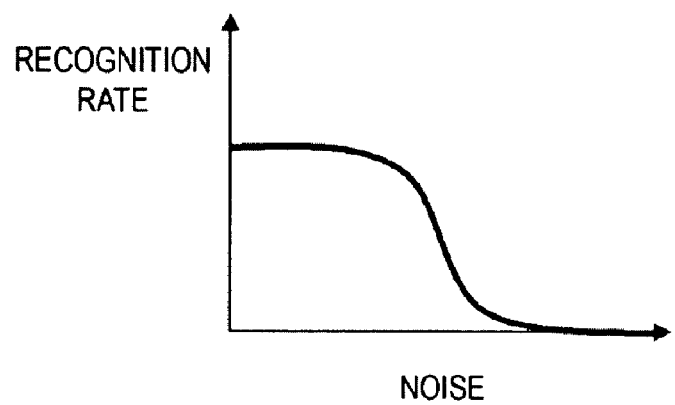
Figure 4C:
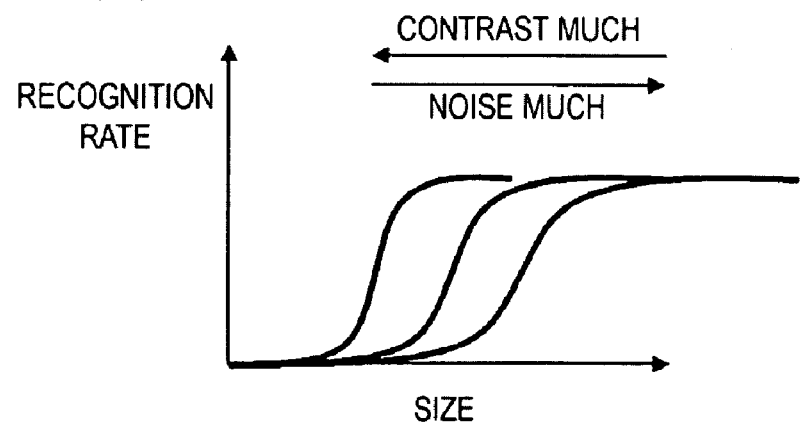
Figure 5:
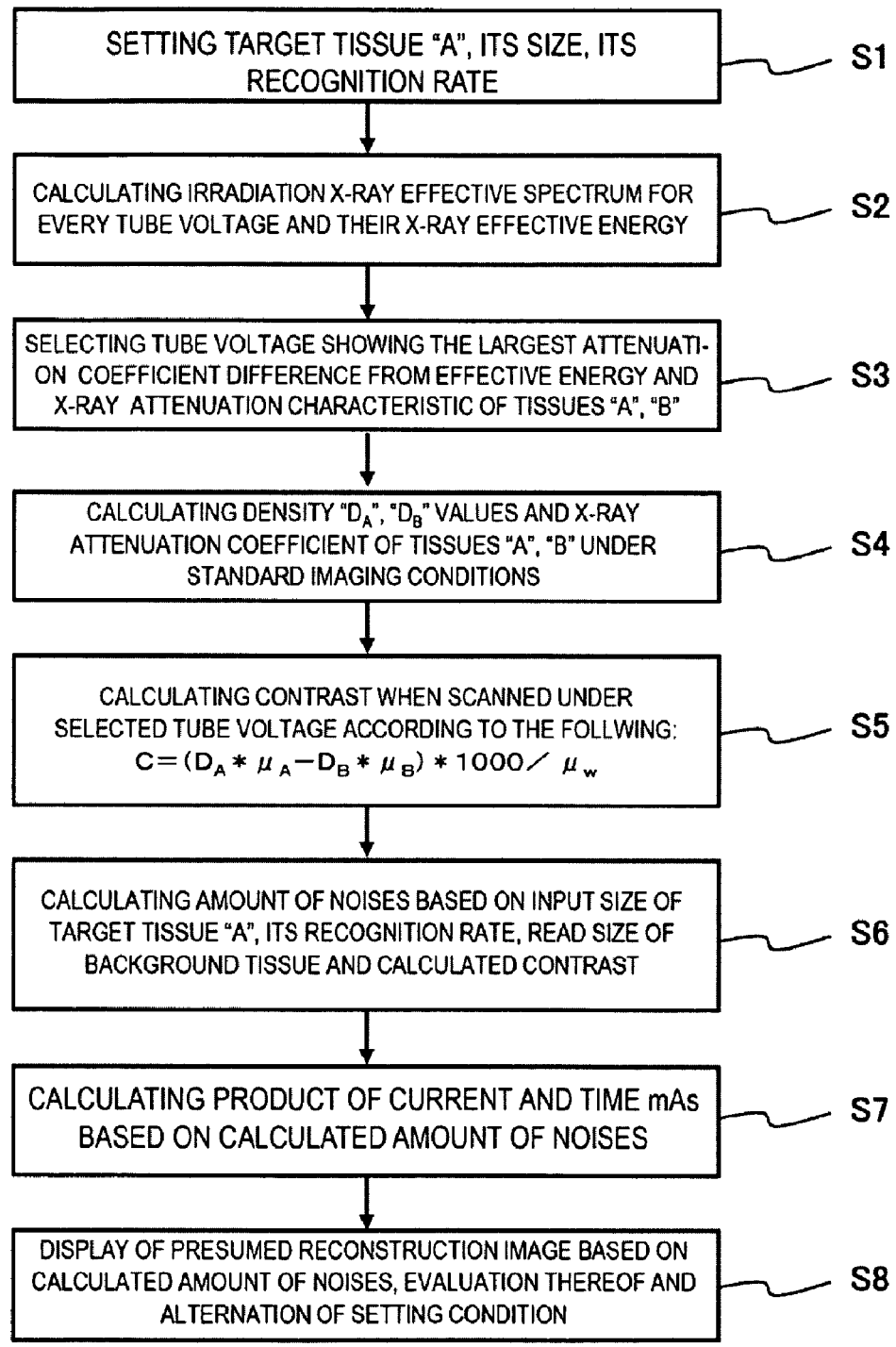
FIG. 5 is a flowchart for explaining steps of computation of scanning conditions and others executed successively in a computing device by making use of data stored in a memory device in FIG. 2 at a scanning planning stage prior to an actual scanning of an inspection portion of an object according to the present invention.

In step S6, by making use of the size of the target tissue A set at step S1, its recognition rate, the size of the background tissue B read from the database in the memory device 313 based on the size of the target tissue A and the contrast C between the target tissue A and the background tissue B calculated at step S5 according to the tube voltage selected at step S3, and according to a formula relating to the recognition rate D of the target tissue A, the sizes $S_A$, $S_B$ of the target tissue A and the background tissue B converted into pixel numbers thereof, the contrast C between the target tissue A and the background tissue B and amount of noises $\sigma_A$, $\sigma_B$ of the target tissue A and the background tissue B or the approximation curves defining these relationships as exemplified in FIGS. 4(a), 4(b) and 4(c), the respective amounts of noises $\sigma_A$, $\sigma_B$ of the target tissue A and the background tissue B are calculated.

In step S7, based on the amount of noises calculated at step S6, a product of tube current and time mAs defining X-ray irradiation dose irradiated from the X-ray generation device 11. The calculation sequence of mAs will be explained with reference of FIG. 10 below.

A scanogram image 101 is acquired through a scanogram scanning 100. For every one line of 101a and 101b perpendicular to the body axis of the scanogram image 101, the maximum value b of projection value 102 and the integrated value RS of the projection value are determined, and an elliptical model approximating a human body 103 having major axis A and minor axis B (an elliptical body of a homogenous material having attenuation coefficient near a human body) is estimated. The attenuation coefficient $\mu_P$ of the elliptical model approximating human body is determined by taking into account of the effective spectra corresponding to the selected tube voltage. The irradiation dose mAs (tube current×circumferential rotating speed) is determined based on the lengths (A, B) of major axis and the minor axis of the elliptical model approximating human body 103, a helical pitch, a view weight for reconstruction, a reconstruction filter and the amount of noises calculated at step S7. More specifically, at first, a penetration distance $l_P(\theta)$ of X-ray beams irradiated from circumferential rotating phase $\theta$ and passing through the center of the elliptical model approximating a human body 103 is calculated based on the following formula (5);

$$l_P(\theta) = A \times B / \text{sqrt}(A^2 \cos^2\theta + B^2 \sin^2\theta) \quad (5)$$

Figure 10:
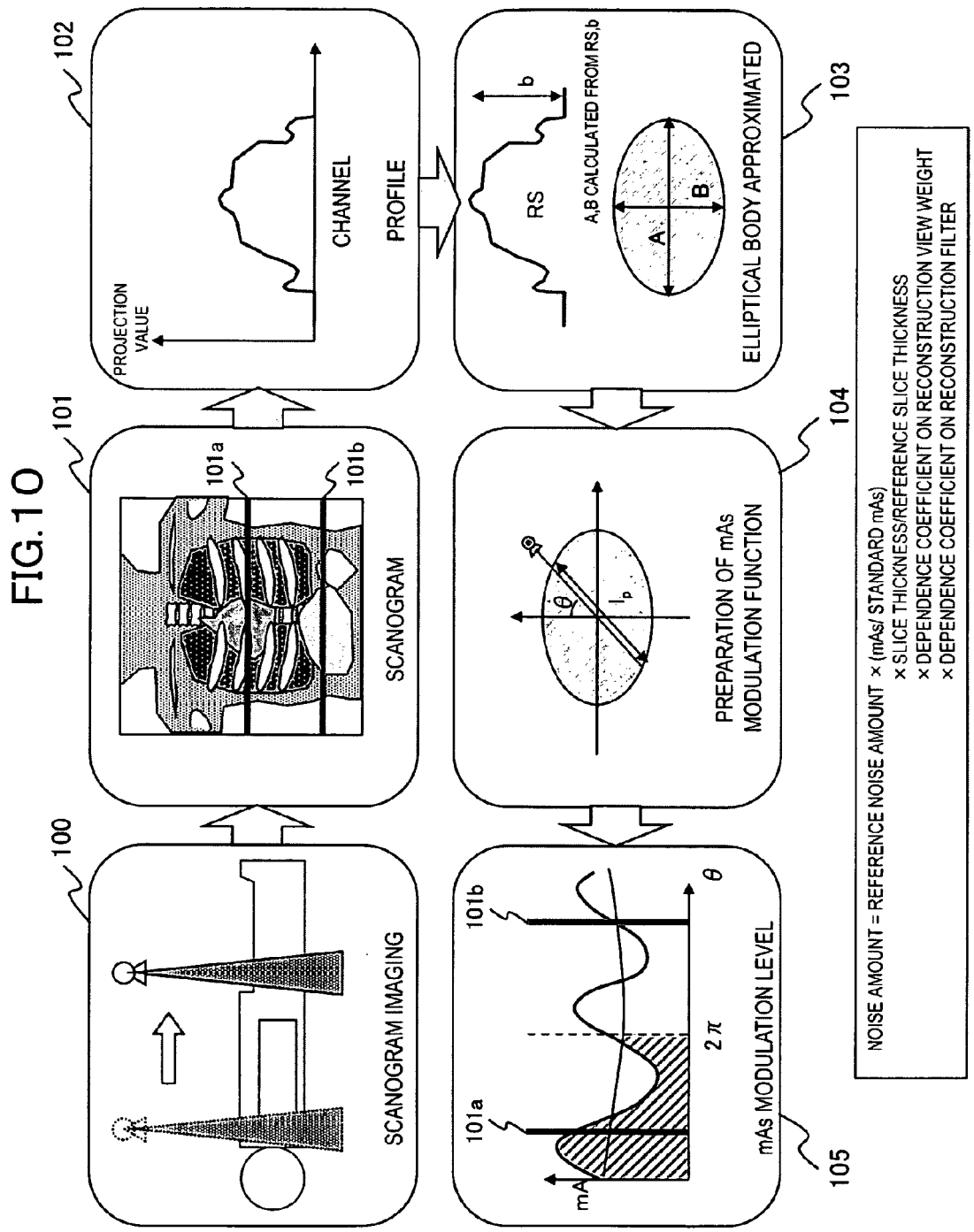
FIG. 10 is a diagram for explaining scanogram scanning of an object for specifying a tomographic scanning position of the object and for determining an elliptical body approximating the cross sectional size of the object at the specified scanning position at the initial scanning planning stage prior to an actual scanning and product of tube current and time mAs defining irradiation dose of the X-ray generation device which is computed thereafter based on the determined approximating elliptical body and noise amount determined in step S6 in FIG. 5.

Subsequently, based on the calculated penetration distance $l_P(\theta)$, a function (104) of modulating mAs ($\theta$) in circumferential rotating direction is produced by modifying the equation shown in FIG. 10 so that noises (dispersion value $\sigma^2$) as defined by formula (6) and corresponding to the amount of noises calculated at step S6 is kept constant. 105 schematically shows a level variation of the tube current, when a helical scan is performed in the direction from line 101a to 101b on the scanogram.

$$\sigma^2 = \sigma_{base}^2 \times C_{ST} \times C_{mAs} \times C_L \times C_{RW} \times C_{RF} \quad (6)$$

Wherein $\sigma_{base}^2$, $C_{ST}$, $C_{mAs}$, $C_L$, $C_{RW}$ and $C_{RF}$ are terms for taking into accounts of the influences when the slice thickness, irradiation dose (tube current×circumferential rotating speed), penetration distance view weight for reconstruction and reconstruction filter are respectively changed and are determined according to the following formulas (7);

$$C_{ST} = ST_{base}/ST$$

$$C_{mAs} = \Sigma\{mAs_{base}/mAs(\theta)\}$$

$$C_L = \Sigma \exp(\mu_P(l_P(\theta) - l_{base}))$$

$$C_{RW} = \Sigma\{W(\theta)^2\}/\{\Sigma W(\theta)\}_2$$

$$C_{RF} = \sigma_{RF}^2/\sigma_{RFbase}^2 \quad (7)$$

Wherein $l_{base}$, $mAs_{base}$ and $ST_{base}$ are respectively a reference diameter of circular model approximating human body, a reference irradiation dose (tube current×circumferential rotating speed) and a reference slice thickness, $W(\theta)$ is a view weight for reconstruction, $\theta$ is a view phase (circumferential rotating phase), $\sigma_{base}^2$ is noises (variance value) acquired from an image obtained by reconstructing around 360 degrees projection data imaged under a condition of $l_{base}$, $mAs_{base}$ and $ST_{base}$ without applying view weight, and $\sigma_{RF}^2$, $\sigma_{RFbase}^2$ are respectively noises of the reconstruction filter and noises of a reference reconstruction filter. Further, when no view weight for reconstruction is applied, $C_{RW}$ is 1, and when view weight for reconstruction is applied, the value increases. Although not specifically explained herein, the view weight for reconstruction relates to the helical pitch, and in case when the helical pitch is large, since the amount of data usable for the reconstruction decreases, $C_{RW}$ enlarges. Further, when defining a generally used reconstruction filter for stomach as a reference, $C_{RW}$ of the same is 1 and that of a filter of which high frequency components are intensified is larger than 1.

When scanning a plurality of portions once through a helical scanning and required to vary noises according to the portions, if a plurality of lines (for every portions) for defining noises are set and $\sigma_{base}^2$, $l_{base}$ are varied at the lines set, the predetermined irradiation dose (tube current×circumferential rotating speed) can be achieved while maintaining the target recognition rate.

Further, with regard to the irradiation dose control based on the amount of noises, the present invention is not limited to the above method but can use any other methods such as conventional methods.

In step S8, from a plurality of standard projection data for every respective inspection portions of a human body imaged under a standard condition and stored in the database within the memory device 313, a standard data of a body type being close to the projection value of the scanogram of the object imaged previously is selected, the size of the selected projection data is corrected based on the integration value of the projection value of the scanogram, the pseudo projection data of the target tissue having the size inputted at step S1 is superposed on the size corrected standard projection data, the respective amounts of noises calculated previously at step S6 and converted into projection data are added on the standard projection data being superposed of the pseudo projection data and the standard projection data to which the noises converted into projection data are added and on which the pseudo projection data are superposed are displayed on the display device 312 as a presumed reconstruction image of the target tissue in recognition rate of 80% for serving the evaluation by an operator (herein, when converting the amount of noises calculated at step S6 into those in the projection data, it is sufficient if a relationship between projection data obtained by scanning such as water phantoms having various sizes in advance and values of image noises at those moments is prepared as a function and the amount of noises to be added to the projection data is determined based on the prepared function).

Figure 11:
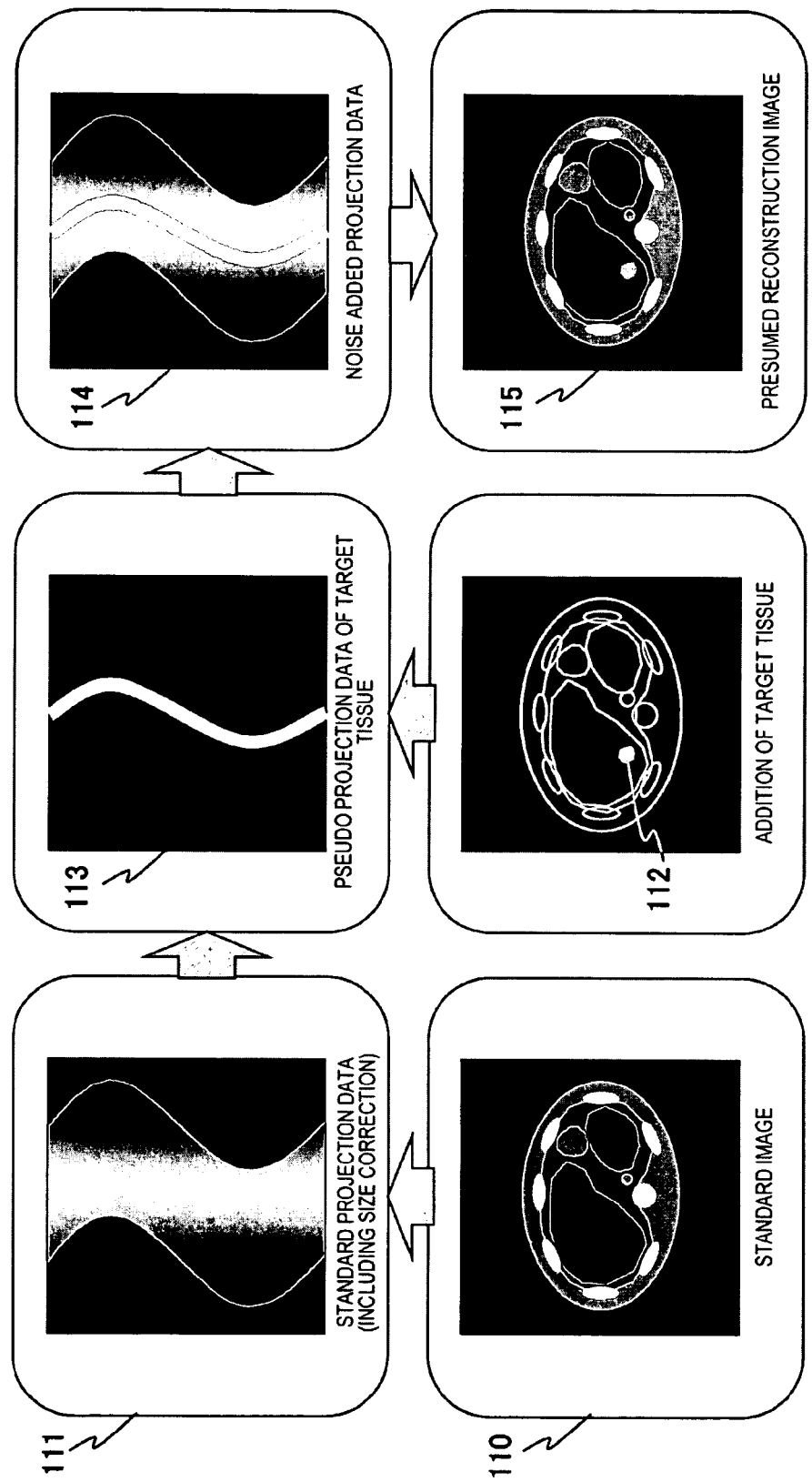
FIG. 11 is a diagram for explaining production of standard image data from standard projection data for every inspection portions stored in the data base in the memory device, superposition of pseudo projection data of the target tissue over the standard projection data, addition of noises of the amount determined according to step 6 in FIG. 5 on the standard projection data superposed of the pseudo projection data of the target tissue and production of a presumed reconstruction image reconstructed from the standard projection data added of the noises and superposed of the pseudo projection data of the target tissue.

The points as has been explained hitherto will be explained specifically with reference to FIG. 11. 111 shows the size corrected standard projection data. 110 is the standard image when the size corrected standard data are reconstructed. 112 is the target tissue added by a user via the input device such as an mouse at an arbitrary position in the inspection portion on the reconstructed standard image 110 of which contour is emphasized, and the size of the target tissue corresponds to the size inputted at step S1. 113 is the pseudo projection data of the target tissue produced based on the added target tissue 112. 114 is the projection data in which the pseudo projection data 113 of the target tissue are superposed on the size corrected standard data 111 and further added thereon respective amounts of noises calculated at step S6 after being converted into projection data. 115 is the presumed reconstruction image of the inspection portion including the target tissue having recognition rate of 80% and the background tissue which are reconstructed from the projection data 114 according to the reconstruction condition set previously, and the presumed reconstruction image corresponds to the presumed reconstruction image 123 as shown in FIG. 6.

The user evaluates the presumed reconstruction image 123 displayed on the screen 120, and when the user satisfies the image, the user pushes the execution button to move to the actual scanning operation according to the set condition. When the user dissatisfies the image, the user modifies such as the recognition rate, the size of the target tissue, the reconstruction condition and the contrast scanning condition that were inputted and set previously, and repeats steps S1 through S8.

As in the above manner, since the operator can recognize before the actual scanning the visibility of the target tissue from the presumed image presumed from the set scanning condition, erroneous settings of the scanning condition can be decreased, possible exposure of the object due to scanning once again is avoided and further diagnosis accuracy can be enhanced.

Further, different from a method that simply adds noises on a reconstructed image, in the present embodiment, since noises corresponding to the data value of the projection data are added, an image having quality further close to the actual one (with regard to such as noises and artifacts) can be obtained.

Further, herein, the data actually imaged of a human body are used as standard data, an virtual human body model produced from computer simulation and phantom data used for evaluating image quality and spatial resolution can be used.

As other usages of the present invention, the present invention can be used to determine an optimum scanner constitution by evaluating the effects of such as compensating filters and copper filters of different shapes and materials by means of the presumed image or the recognition rate. In this instance, the determination can be realized by preparing a plurality of compensating filters, copper filters and lead filters for the scanner, and exchanging the filter depending on the setting. Further, the present invention can be used to determine an optimum reconstruction condition by changing the shape of reconstruction filter depending on the set parameter and evaluating the effect of the reconstruction filter by means of the presumed image or the recognition rate. As will be understood from the above, the present invention can be used as a simulator for optimizing the scanning condition, the device condition, the contrast scanning condition and the reconstruction condition.

Further, the present invention is not limited to the above embodiments and can be carried out by modifying in a variety of manners within a range not exceeding the gist of the present invention. For example, in the above embodiment, as an index how accurately the target tissue is discriminated, the ratio of the portion of the normal distribution of the target tissue not overlapped with the normal distribution of the background tissue to the normal distribution of the target tissue is introduced which is defined as the discrimination capability, however, the present invention is not limited to such index as defined. For example, when data are obtained and stored in advance in what relationship between the normal distributions representing pixel distributions of the target tissue and the background tissue on the histograms as shown in FIG. 4, TPF (True Positive Fraction) in ROC analysis gives such as 0.8, it is needless to say that the amount of noises (amount of standard deviation) for giving TPF of 0.8 can be determined based on the stored data. Further, it is also needless to say that the function expressing the pixel distribution is not limited to the normal distribution but can be Poisson distribution.

The invention claimed is:

1. An X-ray CT apparatus comprising:
an X-ray generating means;
an X-ray detector disposed opposing to the X-ray generating means;
a rotating means for rotating the X-ray generating means and the X-ray detector in a circular orbit of a same rotation center;
a control means for controlling the X-ray generating means so as to irradiate X-rays from the X-ray generating means to an object to be examined laid along the rotation center and controlling the X-ray detector to detect X-ray dose penetrated through the object, while controlling the rotating means to rotate the X-ray generating means and the X-ray detector; and
a reconstruction computing means for performing reconstruction computation by making use of the data of the penetrated X-ray dose obtained under the control of the control means and acquiring a tomographic image;
the X-ray CT apparatus further comprising
an input means configured for input of information with respect to a target tissue of the object to be discriminated with a specific recognition rate in the tomographic image, and for input of an index with respect to the specific recognition rate of the discrimination; and
a scanning condition determining means for determining scanning conditions for discriminating the target tissue based on the index inputted by the input means.

2. An X-ray CT apparatus according to claim 1 further comprising:
an apparatus information memory means which stores apparatus characteristics of the X-ray CT apparatus; and
an image condition determining means which determines the scanning conditions by making use of the index, the information relating to the target tissue and the apparatus characteristics.

3. An X-ray CT apparatus according to claim 2, wherein
the apparatus information memory means is configured to store information relating to energy spectra of X-rays irradiated from the X-ray generating means for respective set tube voltage values, and
the image condition determining means is provided with a tube voltage determining means which determines an optimum tube voltage by making use energy spectra of the respective X-rays and X-ray attenuation coefficients of the target tissue and the background tissue.

4. An X-ray CT apparatus according to claim 3, wherein the optimum tube voltage is determined so that the difference between the X-ray attenuation coefficients of the target tissue and the background tissue enlarges.

5. An X-ray CT apparatus according to claim 3, further comprising:
   a density information memory means which stores density information of the target tissue and the background tissue; and
   a contrast determining means which determines a contrast of the target tissue and the background tissue when the tomographic image is taken with the optimum tube voltage determined by the tube voltage determining means based on the density information and the X-ray attenuation coefficients.

6. An X-ray CT apparatus according to claim 5 further comprising:
   an index relating variables and functions group memory means which stores an index relating variables and functions group representing a relationship between the index, the contrast, the amount of noises of the target tissue or the background tissue on the tomographic image and the size of the target tissue on the tomographic image, and
   wherein the scanning condition determining means includes a noise amount calculating means which calculates an amount of noises for discriminating with the index the target tissue having the contrast and the size from the background tissue based on the index relating variables and functions group.

7. An X-ray CT apparatus according to claim 6, further comprising:
   a noise and irradiation dose function memory means which stores a noise and irradiation dose function representing a relationship between the amount of noises and the irradiation dose of X-rays during the scanning,
   wherein the scanning condition determining means includes an irradiation dose calculating means which calculates an irradiation dose of X-rays, and the amount of noises calculated by the noise amount calculating means based on the noise and irradiation dose function is obtained on the tomographic image.

8. An X-ray CT apparatus according to claim 7, the irradiation dose calculating means takes into account during the irradiation dose calculation of differences in X-ray penetration distance passing through the object, a reconstruction view weight and a reconstruction filter.

9. An X-ray CT apparatus according to claim 7 further comprising:
   a tube current determining means which determines a tube current based on an irradiation dose calculated by the irradiation dose calculating means.

10. An X-ray CT apparatus according to claim 6 further comprising:
   a standard human body projection data memory means which stores a standard human body projection data obtained under standard scanning conditions;
   a presumed image preparing means which presumes by making use of the standard human body projection data what type of an image is obtained when the scanning is performed under the scanning conditions determined by the scanning condition determining means; and
   a display means which displays the image obtained when the scanning is performed.

11. An X-ray CT apparatus according to claim 10, wherein the presumed image preparing means comprises
   a superposing means which superposes pseudo projection data representing the target tissue on the standard human body projection data,
   a noise adding means which converts the amount of noises calculated by the noise amount calculating means into projection data and adds the same thereon, and
   means for preparing the presumed image by performing reconstructing computation of the data obtained by the noise adding means.

12. An X-ray CT apparatus according to claim 11 further comprising:
   a scanogram scanning means which images a projection image of the object from the side face thereof,
   wherein the presumed image preparing means includes an object size calculating means which calculates the size of the object actually imaged based on the scanogram image obtained by the scanogram scanning means and prepares the presumed image by taking into account of the calculated size.

13. An X-ray CT apparatus according to claim 12, wherein the presumed image preparing means performs correction of the size of the standard human body projection data based on the calculated size and prepares the presumed image by making use of the data after the correction.

14. An X-ray CT apparatus according to claim 10, wherein in response to at least any one of set parameters determined by the scanning condition determining means being modified, the image presumed by the presumed image preparing means is altered and the altered image is displayed on the display means.

15. An X-ray CT apparatus according to claim 6, wherein the index is a true positive rate defined in ROC analysis, and
   the noise amount calculating means is comprised with includes a true positive rate and noise amount function memory means which stores in advance a true positive rate and noise amount function showing how much amount of noises is sufficient for obtaining a predetermined true positive rate for the determined contrast and calculates amount of noises by making use of the true positive rate and noise amount function.

16. An X-ray CT apparatus according to claim 3 further comprising:
   an X-ray attenuation coefficient memory means at a time of contrast medium injection which stores X-ray attenuation coefficients of the target tissue and the background at respective time phases after a contrast medium is injected into the object,
   wherein the value of the tube voltage is decided to be the best value based on the X-ray attenuation coefficients stored in the X-ray attenuation memory means.

17. An X-ray CT apparatus according to claim 1,
   wherein the information relating to the target tissue inputted by the input means includes size and type of the target tissue, and
   the X-ray CT apparatus further comprises an X-ray attenuation coefficient memory means which stores X-ray attenuation coefficients of the target tissue and a background tissue disposed around the target tissue.

18. An X-ray CT apparatus according to claim 1, wherein the index is expressed by a discrimination capability defined, when pixel distributions of the target tissue and the background tissue are illustrated in histograms, by a ratio of a portion of the pixel distribution of the target tissue not overlapping with the pixel distribution of the background tissue with respect to the pixel distribution of the target tissue.

19. An X-ray CT apparatus according to claim 18, wherein the pixel distribution is approximated by a normal distribution or a Poisson distribution.

20. A scanning condition determining method for an X-ray CT apparatus comprising:

(1) a step of inputting information with respect to a target tissue to be discriminated in a tomographic image to be acquired by the X-ray CT apparatus and an index with respect to correctness of the discrimination, and (2) a step of determining scanning conditions for discriminating the target tissue with the index based on the information with respect to the target tissue, the index and apparatus characteristics of the X-ray CT apparatus.

* * * * *